United States Patent [19]

Child et al.

[11] Patent Number: 5,071,627

[45] Date of Patent: Dec. 10, 1991

[54] REACTOR SYSTEM FOR CONDUCTING A CHEMICAL CONVERSION

[75] Inventors: Jonathan E. Child, Sewell; Byung C. Choi; Francis P. Ragonese, both of Cherry Hill, all of N.J.

[73] Assignee: Mobil Oil Corp., Fairfax, Va.

[21] Appl. No.: 445,304

[22] Filed: Dec. 4, 1989

[51] Int. Cl.[5] ............................................... B01J 8/02
[52] U.S. Cl. .................................... 422/196; 165/154; 165/179; 165/185; 165/907; 422/188; 422/198; 422/201; 422/202; 422/203; 422/205
[58] Field of Search ............... 165/154, 179, 185, 907; 422/198, 201, 202, 203, 205, 188, 193, 196, 206, 214, 223

[56] References Cited

U.S. PATENT DOCUMENTS

| | | |
|---|---|---|
| 2,162,913 | 6/1939 | Eversole et al. . |
| 2,472,254 | 6/1949 | Johnson ............................... 422/217 |
| 2,477,380 | 7/1949 | Kreps et al. . |
| 2,499,304 | 2/1950 | Evans ................................... 422/223 |
| 2,797,247 | 6/1957 | Keith . |
| 2,798,097 | 7/1957 | Hettinger, Jr. et al. . |
| 2,805,260 | 9/1957 | Keith . |
| 2,830,090 | 4/1958 | Teter et al. . |
| 2,861,045 | 11/1958 | Langer, Jr. . |
| 2,891,999 | 6/1959 | Langer, Jr. . |
| 2,986,454 | 5/1961 | Jewett ................................. 422/205 |
| 3,006,970 | 10/1961 | Beuther et al. . |
| 3,198,752 | 8/1965 | Bridger et al. . |
| 3,409,075 | 11/1968 | Long .................................... 165/154 |
| 3,516,800 | 6/1970 | Yamamoto et al. ................. 422/205 |
| 3,595,310 | 7/1971 | Burne et al. ........................ 165/161 |
| 3,732,919 | 5/1973 | Wilson ................................ 165/907 |
| 3,810,849 | 5/1974 | Massie . |
| 3,973,718 | 8/1976 | Deschamps ......................... 165/907 |
| 3,989,762 | 11/1976 | Ester . |
| 4,042,633 | 8/1977 | Woods . |
| 4,182,914 | 1/1980 | Imaizumi . |
| 4,214,107 | 7/1980 | Chang et al. . |
| 4,250,147 | 2/1981 | Jensen . |
| 4,334,890 | 6/1982 | Kochar et al. . |
| 4,345,644 | 8/1982 | Dankowski ......................... 165/154 |
| 4,368,777 | 1/1983 | Grasso ................................ 165/154 |
| 4,418,219 | 11/1983 | Hanes et al. . |
| 4,499,313 | 2/1985 | Okumura et al. . |
| 4,605,787 | 8/1986 | Chu et al. . |
| 4,714,787 | 12/1987 | Bell et al. . |
| 4,783,555 | 11/1988 | Atkins . |
| 4,889,181 | 12/1989 | Meijer ................................ 165/154 |
| 4,893,670 | 1/1990 | Joshi et al. ......................... 165/154 |

FOREIGN PATENT DOCUMENTS

| | | |
|---|---|---|
| 0055045 | 6/1982 | European Pat. Off. . |
| 133661 | 1/1979 | Fed. Rep. of Germany . |
| 25345 | 2/1984 | Japan . |
| 0246335 | 12/1985 | Japan . |

OTHER PUBLICATIONS

Smith, "Chemical Eng. Kinetics, 3rd Ed.", McGraw-Hill Book Company p. 351, 1981.

Primary Examiner—Robert J. Warden
Assistant Examiner—Timothy M. McMahon
Attorney, Agent, or Firm—Alexander J. McKillop; Charles J. Speciale; Lori F. Cuomo

[57] ABSTRACT

A reactor system and process for conducting exothermic or endothermic chemical reactions achieves greater kinetic efficiency through transfer of heat between adjacent feed temperature modification and reaction zones.

10 Claims, 3 Drawing Sheets

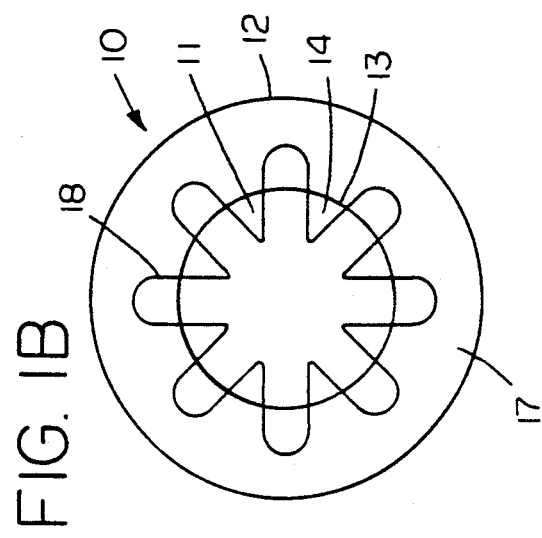
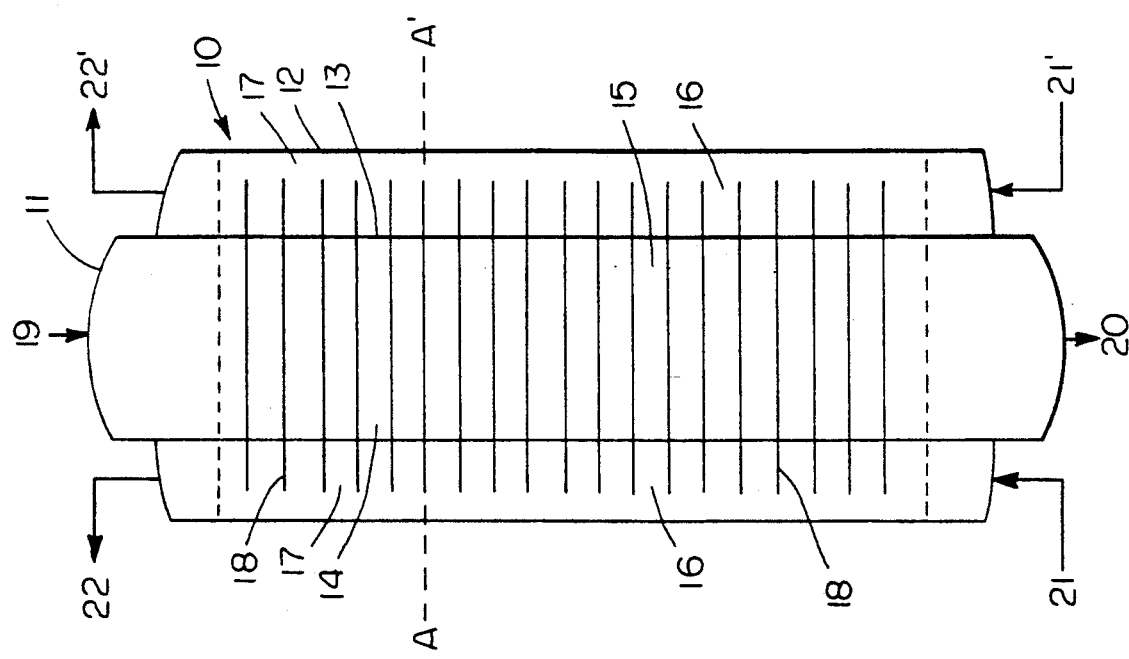

REACTOR SYSTEM FOR CONDUCTING A CHEMICAL CONVERSION

CROSS-REFERENCE TO RELATED APPLICATIONS

This application is related by subject matter to commonly assigned, copending U.S. patent applications Ser. Nos. 139,566, filed Dec. 30, 1987; 336,504, filed Apr. 11, 1989; 414,630, filed Sept. 26, 1989; and 279,615, filed Dec. 5, 1988. The contents of these applications, which are concerned with the production of alcohol(s) and/or ether(s), are incorporated by reference herein.

BACKGROUND OF THE INVENTION

This invention relates to a chemical reactor system for conducting endothermic reactions such as catalytic reforming and exothermic reactions such as the hydration and/or etherification of olefins to provide one or more alcohols, ethers or mixtures thereof.

There is a need for an efficient catalytic reactor and process for the manufacture of alcohols and ethers from light olefins thereby augmenting the supply of high octane blending stocks for gasoline. Lower molecular weight alcohols and ethers such as isopropyl alcohol (IPA) and diisopropyl ether (DIPE) are in the gasoline boiling range and are known to have a high blending octane number. In addition, by-product propylene from which IPA and DIPE can be made is usually available in a fuels refinery. The petrochemicals industry also produces mixtures of light olefin streams in the $C_2$ to $C_7$ molecular weight range and the conversion of such streams or fractions thereof to alcohols and/or ethers can also provide products useful as solvents and as blending stocks for gasoline.

The catalytic hydration of olefins to provide alcohols and/or ethers is a well-established art and is of significant commercial importance. Representative olefin hydration processes are disclosed in U.S. Pat. Nos. 2,162,913; 2,477,380; 2,797,247; 2,798,097; 2,805,260; 2,830,090; 2,861,045; 2,891,999; 3,006,970; 3,198,752; 3,810,849; 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g. ZSM-5, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of from 20 to 500. The use of such a catalyst is said to result in higher yields of alcohol than olefin hydration processes which employ conventional solid acid catalyst. Use of the catalyst is said to offer the advantage over ion-exchange type olefin hydration catalysts of not being restricted by the hydration temperature.

U.S. Pat. No. 4,783,555 describes an olefin hydration process employing a medium pore zeolite as hydration catalyst. Specific catalysts mentioned are Theta-1, said to be preferred, ferrierite, ZSM-22, ZSM-23 and NU-10. Nu-10, Theta-1 and ZSM-22 are known to have the same structure.

Japanese Laid-Open Patent Application No. 60-246335 discloses the hydration of branched olefins to alcohols in the presence of a zeolite having a silica to alumina ratio of above 10.

The catalyzed reaction of olefins with alcohols to provide ethers is another well known type of process.

As disclosed in U.S. Pat. No. 4,042,633, diisopropyl ether (DIPE) is prepared from isopropyl alcohol (IPA) employing montmorillonite clay catalysts, optionally in the presence of added propylene.

U.S. Pat. No. 4,182,914 discloses the production of DIPE from IPA and propylene in a series of operations employing a strongly acidic cation exchange resin as catalyst.

In U.S. Pat. No. 4,334,890, a mixed $C_4$ stream containing isobutylene is reacted with aqueous ethanol to form a mixture of ethyl tertiary butyl ether (ETBE) and tertiary butyl alcohol (TBA).

U.S. Pat. No. 4,418,219 discloses a process for preparing methyl tertiary butyl ether (MTBE) by reacting isobutylene and methanol in the presence of boron phosphate, blue tungsten oxide or a crystalline aluminosilicate zeolite having a silica to alumina mole ratio of at least 12:1 and a Constraint Index of from 1 to about 12 as catalyst.

As disclosed in U.S. Pat. No. 4,605,787, alkyl tert-alkyl ethers such as MTBE and tertiary amyl methyl ether (TAME) are prepared by the reaction of a primary alcohol with an olefin having a double bond on a tertiary carbon atom employing as catalyst an acidic zeolite having a Constraint Index of from about 1 to 12, e.g., ZSM-5, ZSM-11, ZSM-12, and ZSM-23.

U.S. Pat. No. 4,714,787 discloses the preparation of ethers by the catalytic reaction of linear monoolefins with primary or secondary alcohols employing, as catalyst, a zeolite having a pore size greater than 5 Angstroms, e.g. ZSM-5, zeolite Beta, zeolite X, zeolite Y, etc. Specifically, in connection with the reaction of propylene with methanol to provide methyl isopropyl ether (MIPE), effluent from the reactor is separated into a MIPE fraction, useful as a gasoline blending component, with unreacted propylene, methanol, by-product dimethyl ether (DME) and water at up to one mole per mole of by-product DME, either individually or in combination, being recycled to the reactor.

In European Patent Application 55,045, an olefin is reacted with an alcohol to provide an ether, e.g., isobutene and methanol are reacted to provide MTBE, in the presence of an acidic zeolite such as zeolite Beta, ZSM-5, ZSM-8, ZSM-11, ZSM-12, ZSM-23, ZSM-35, ZSM-43 and ZSM-48, and others, as catalysts.

German Patent No. 133,661 describes the reaction of isobutene and methanol to provide a mixture of products including MTBE, butanol and isobutene dimer employing acidic zeolite Y as catalyst.

Japanese Laid-open Patent Application No. 59-25345 describes the reaction of a primary alcohol with a tertiary olefin in the presence of a zeolite having a silica to alumina mole ratio of at least 10 and the X-ray diffraction disclosed therein to provide a tertiary ether.

SUMMARY OF THE INVENTION

It is an object of the present invention to provide a reactor system for an endothermic or exothermic chemical reaction offering greater kinetic efficiency.

It is a particular object of the invention to provide a reactor system for carrying out an exothermic chemical conversion in which heat of reaction is utilized to preheat feed and simultaneously reduce the temperature rise of the chemical conversion reaction.

It is another specific object of the invention to provide a chemical reactor and process for the hydration and/or etherification of olefin to provide alcohol(s), ether(s) or their mixtures which are useful, among other applications, as high octane blending stocks for gasolines.

In keeping with these and other objects of the invention, there is provided a reactor system for conducting a chemical conversion reaction which comprises:

a) a first reactor sub-unit possessing a feed temperature modification zone and a reaction zone;

b) a second reactor sub-unit possessing a feed temperature modification zone and a reaction zone;

c) first heat transfer means for either transferring heat from the reaction zone of the first reactor sub-unit to the feed temperature modification zone of the second reactor sub-unit when the reaction occurring in said reaction zone is exothermic or transferring heat to the reaction zone of the first reactor sub-unit from the feed temperature modification zone of the second reactor sub-unit when the reaction occurring in said reaction zone is endothermic; and, d) second heat transfer means for either transferring heat from the reaction zone of the second reactor sub-unit to the feed temperature modification zone of the first reactor sub-unit when the reaction occurring in said reaction zone is exothermic or transferring heat to the reaction zone of the second reactor sub-unit from the feed temperature modification zone of the first reactor sub-unit when the reaction occurring in said reaction zone is endothermic.

Applied, for example, to the operation of an exothermic reactor, feed is introduced into the temperature modification zone of one reactor sub-unit where its temperature is increased as a result of acquiring heat provided by the exotherm occurring within the reaction zone of the other reactor sub-unit. Not only does this arrangement make effective use of heat of reaction to improve the kinetic efficiency of the particular chemical conversion being conducted, by significantly reducing the temperature rise occurring in the reaction zone of each reactor sub-unit, it also provides effective temperature management and limits the possibility of excessive temperature excursions within the reactor which could lead to reduced yield of desired product(s) and even reactor shut-down.

BRIEF DESCRIPTION OF THE DRAWINGS

FIGS. 1A and 1B are, respectively, a schematic side elevation view and a plan view (taken through line A—A' of FIG. 1) of one embodiment of a chemical reactor system in accordance with the present invention; and, FIGS. 2A and 2B and 3A and 3B are, respectively, schematic side elevation and plan views of additional reactor arrangements in accordance with this invention.

DESCRIPTION OF THE PREFERRED EMBODIMENTS

Figure 2B:
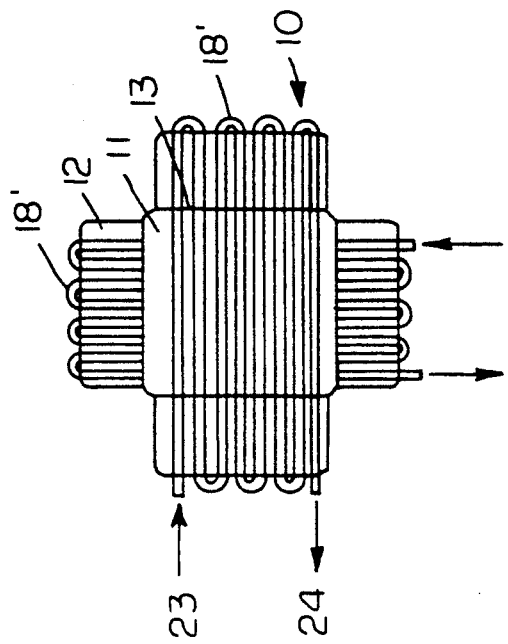

The chemical reactor system and process of the present invention are generally applicable to carrying out any chemical conversion. Thus, the reactor system and process herein can be used for carrying out endothermic conversions of which catalytic reforming is a particularly important example and exothermic reactions such as hydrocracking, hydrotreating, oxidation, e.g., oxidative coupling, the conversion of methanol to gasoline, olefin oligomerization, etc. The chemical reactor system and process of this invention will be particularly described herein in connection with the operation of an exothermic chemical conversion, namely, the catalytic hydration/etherification of individual light olefins and mixtures of light olefins of various structures, preferably within the $C_{2-7}$ range, to provide alcohols and/or ethers. Accordingly, the invention is especially applicable to the hydration/etherification of ethylene, propylene, butenes, pentenes, hexenes, heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, a typical FCC light olefin stream possesses the following composition:

| Component | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

The reactor system and process of the invention is particularly advantageous for the conversion of propylene and propylene-containing streams to mixtures of IPA and DIPE.

Lower alcohols which are suitable for reaction with olefin herein, optionally together with water, include alcohols having from 1 to about 6 carbon atoms, i.e., methanol, ethanol, propanol, isopropyl alcohol, n-butanol, sec-butanol, tert-butanol, the pentanols and the hexanols.

When olefin is reacted with water to provide an alcohol, the reaction can be regarded as one of hydration although, of course, some product alcohol can, and does, react with olefin feed to co-produce ether. When olefin is reacted solely with alcohol to provide an ether, the reaction can be regarded as one of etherification. When olefin is reacted with both water and alcohol to provide a mixture of alcohol and ether, the resulting conversion involves both hydration and etherification reactions. In addition, other reactions such as the chemical dehydration of alcohol to ether may occur to some extent. For the sake of convenience, the expression "olefin hydration" is used herein to apply to any and all of these reactions.

As shown in FIGS. 1A and 1B, olefin hydration reactor system 10 possesses an inner, or core, reactor sub-unit 11 surrounded by an outer reactor sub-unit 12 sharing a common wall 13 with reactor sub-unit 11. Reactor sub-unit 11 is divided into a feed preheating zone 14 and an olefin hydration reaction zone 15 and reactor sub-unit 12 is divided into a feed preheating zone 16 and an olefin hydration reaction zone 17 (the dotted lines demarcating these zones). Heat transfer means provided as heat conducting rod elements 18 extend from the core reactor sub-unit to the outer reactor sub-unit. Due to the arrangement of the inner reactor sub-unit being surrounded by the outer reactor sub-unit, heat of reaction is transferred from olefin hydration reaction zones 15 and 17 to feed preheating zones 14 and 16, respectively, partly through common reactor wall 13 and partly by means of heat conducting rod elements 18 which traverse all of these zones. Heat conducting rod elements 18 are preferably finned to provide greater heat transfer area and are advantageously fabricated from a material exhibiting high thermal conductivity, e.g., copper, aluminum, etc. Feed preheating zones 14 and 16 can be filled with any known and conventional inert packing material to promote heat transfer to the feed introduced therein. Suitable packing materials include ceramic, quartz, stainless steel, Raschig rings, etc. Feed (i.e., olefin and water and/or alcohol) are introduced through line 19 into preheating zone 14 of inner reactor sub-unit 11. Picking up heat of reaction from surrounding olefin hydration reaction zone 17 of outer reactor sub-unit 12, the pre-heated feed passes downwardly into olefin hydration reactor zone 15 wherein the catalyzed exothermic conversion of olefin to product alcohol(s) and/or ether(s), recovered through line 20, takes place. Some of the heat of reaction produced in zone 15 is transferred to, and taken up by, feed (which may be the same or different in composition from the feed introduced into preheating zone 14) introduced to preheating zone 16 through lines 21 and 21'. In a reverse of the sequence described in connection with inner reactor sub-unit 11, preheated feed passes upwardly from pretreatment zone 12 to enter olefin hydration reaction zone 17, the product alcohol(s), ether(s) or mixture thereof being recovered through lines 22 and 22'.

It will, of course, be recognized, that the maximum temperature differentials in the reactor system exist at the extreme top and bottom sections thereof and therefore the maximum heat transfer from one zone to an adjacent zone will take place in these sections. Conversely, a minimum temperature differential exists within the middle section of the reactor and little, if any, heat transfer may be effected in this region.

Figure 2A:
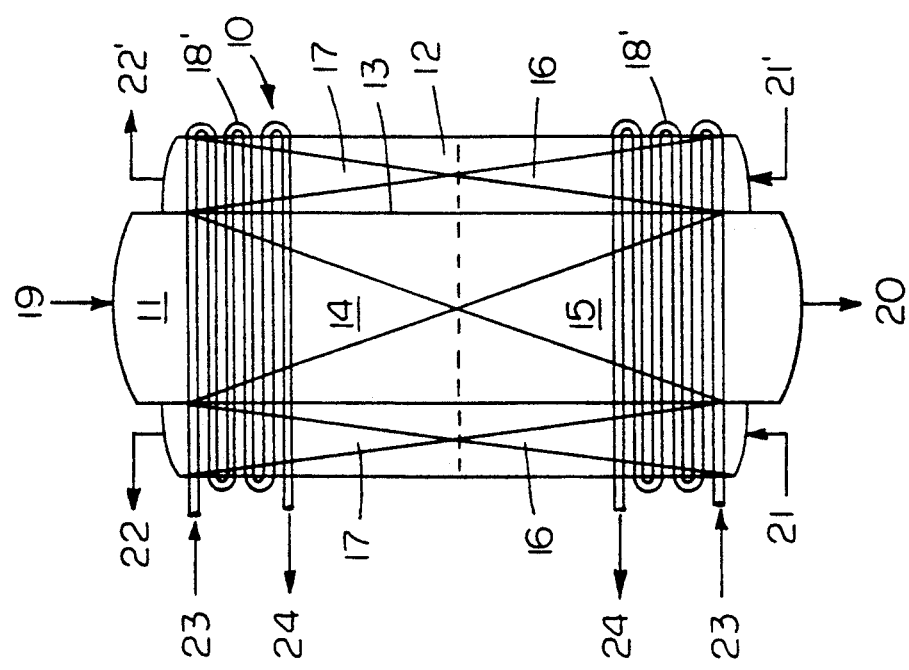

Reactor system 10 shown in FIGS. 2A and 2B is similar in design and operation to the embodiment of FIGS. 1A and 1B except that in place of heat conducting rod elements 18 of the latter, conduits, or coils, 18' are provided for conveying a fluid heat exchange medium, e.g., water, ethylene glycol, Dowtherm, eutectic salts, etc., between the reaction zone of one reactor sub-unit and the adjacent feed preheating zone of the other reactor sub-unit. Thus, fluid heat exchange medium introduced into coils 18' at 23 courses through adjacent preheating and reaction zones transferring heat of reaction from the latter to feed introduced into the former, the heat exchange medium thereafter exiting at 24.

In middle region 25 of reactor system 10, indicated in an approximate manner by the dotted lines, there will be a minimum temperature differential and, consequently, minimum heat transfer in this region. As in the case of the heat conducting rod elements of the reactor of FIGS. 1A-B, it is preferred to provide conduits 18' with fins and to construct the conduits of high thermal conductivity material. The choice of fluid heat exchange medium may depend on the temperature of the reaction zones. If water is selected, it may be necessary to subject it to pressure to maintain it in the liquid state.

Figure 3B:
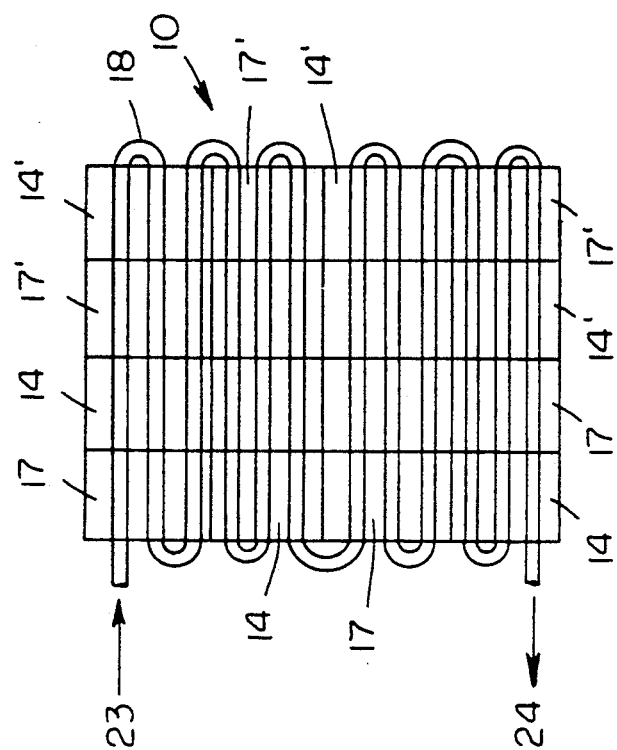
Figure 3A:
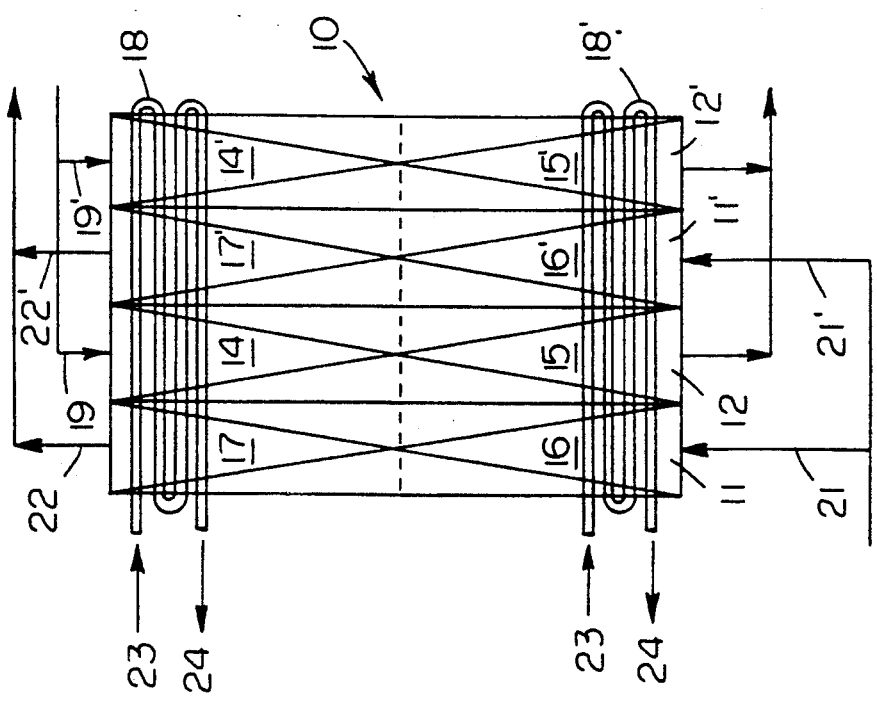

FIGS. 3A and 3B illustrate another embodiment of the reactor system which is similar to that described above in connection with FIGS. 2A and 2B except that in the former there is an alternating, side-by-side arrangement of reactor sub-units 11 and 11' with reactor sub-units 12 and 12'. Otherwise, and similar to the reactor systems illustrated above, feed preheating zones 14, 14', 16 and 16' are arranged adjacent to olefin hydration reaction zones 17, 17', 16 and 16', respectively. Since the number of commonly shared reactor walls, and therefore shared reactor wall surface area, is greatly increased in the configuration shown in FIGS. 3A and 3B, heat transfer through such walls will account for a greater amount of the overall heat transfer occurring in such a reactor system compared with that of the reactor systems of FIGS. 1 and 2.

The operating conditions of the olefin hydration reaction zones within the reactor systems of FIGS. 1-3 are not overly critical. They include a temperature ranging from 50° C. up to about 300° C., preferably from about 80 to about 220° C. and more preferably from about 100° to about 200° C., a total system pressure which is sufficient to maintain the water and/or alcohol in the liquid state, e.g., at least about 100 psig, preferably at least about 300 psig and most preferably at least about 750 psig and a total water and/or alcohol to total olefin mole ratio of from about 0.1 to about 30, preferably from about 0.2 to about 15 and most preferably from about 0.3 to about 5. It may be preferable to operate at low water to total olefin mole ratios as disclosed in U.S. patent application Ser. No. 139,567 referred to above, e.g., at water to total olefin mole ratios of less than about 1.

Reaction times of from about 20 minutes to about 20 hours when operating in batch and a liquid hourly space velocity (LHSV) based on olefin of from about 0.1 to about 10 when operating continuously are suitable. It is generally preferable to recover any unreacted olefin and recycle it to the reactor system.

Those skilled in the art will recognize that selection of specific operating conditions for a particular olefin feed will influence the nature of the hydration/etherification product(s). It will also be appreciated that the precise olefin hydration/etherification conditions selected should, to some extent, reflect the nature of the olefin feed, isoolefins generally requiring milder process conditions than straight chain olefins.

When seeking to maximize the production of ether by the hydration of olefin, the aqueous product effluent recovered from the reactor system herein containing both alcohol and ether reaction products can be introduced into a separator, e.g., a distillation column, for recovery of ether. The dilute aqueous solution of alcohol may be then introduced into a second separator, e.g., another distillation column, where a water/alcohol azeotrope is recovered. A fraction of the azetrope may be fed into a dehydration reactor of conventional or otherwise known type and operation to provide a further quantity of ether which can be combined with the ether previously recovered from the olefin hydration reactor. By blending various product streams, almost any ratio of alcohol/ether can be obtained. When alcohol/ether mixtures are to be used as gasoline blending stocks, this capability for adjusting the ratios of alcohol to ether offers great flexibility in meeting the octane requirements for given gasoline compositions. Regulatory considerations aside, alcohol/ether mixtures, e.g., IPA/DIPE mixtures, can constitute up to about 20 weight percent or so of the gasoline to which they are added.

A particularly advantageous procedure for producing mixtures of alcohol and ether, and in particular IPA and DIPE, from the hydration of an olefin-containing feed (a propylene-containing feed in the case of IPA/DIPE mixtures) employing a large pore zeolite such as zeolite Y or zeolite Beta is described in U.S. patent application Ser. No. 139,543 referred to above. In accordance with this procedure as applied herein, e.g., to the production of IPA/DIPE mixtures, a fresh propane/propylene-containing feed (readily available in many petroleum refineries) and fresh water are cofed, together with recycled unreacted propylene and recycled water from a decanter, into the feed preheating zones of the reactor system of this invention. The reactor effluent is passed to a separator unit with propane and unconverted propylene being recycled to the reactor system, part of the gaseous mixture being purged in order to avoid build-up of propane in the recycle loop. The liquid products from the separator unit are introduced to a distillation unit where an azeotropic mixture of IPA, DIPE, water and propylene oligomers (mostly $C_6$ olefin) is distilled off and, following cooling, is introduced into a decanter in which phase separation takes place. The upper layer contains mostly DIPE, e.g., 90 weight percent or more, and relatively little water, e.g., 1 weight percent or so. The lower layer is largely water containing negligible quantities of IPA and DIPE. The quantity of the decanter overheads which is recycled can be regulated so as to control the water content in the final product. The bottom fraction of the distillation unit, mainly IPA, is combined with DIPE in the decanter overheads to provide the final IPA/DIPE mixture.

Where it is desired to separate out the alcohol from an alcohol/ether mixture and thus provide essentially pure ether, one can advantageously practice the procedure of U.S. patent application Ser. No. 139,566 referred to above. According to this process as applied herein to the production of DIPE, the propylene component of a mixed propane/propylene feed undergoes hydration in the presence of a large pore zeolite olefin hydration catalyst, e.g., zeolite Y or zeolite Beta, present in each reaction zone of the reactor system of this invention with the effluent therefrom being passed to a separator operating below the olefin hydration reaction temperature. There, two liquid phases form, the aqueous phase being removed and recycled to the hydration reactor. The hydrocarbon-rich phase is flashed to a lower pressure to effect separation of the unreacted $C_3$ components. The flashed product, now containing a substantial amount of IPA product, is introduced to a distillation unit operated at or below atmospheric pressure to effect further purification of the DIPE. The azeotropic IPA, DIPE and water overhead product containing a small amount of propylene oligomer is condensed and thereafter contacted with reactor feed water. The resulting phase separation provides a DIPE product containing at most negligible amounts of IPA and water, e.g., 1.0 weight percent and 0.5 weight percent of these materials, respectively. The remaining aqueous phase can be recycled to the olefin hydration reactor system herein.

While any known or conventional olefin hydration/etherification catalyst can be used in the olefin hydration reaction zones of the reactor system herein, it is especially advantageous to employ a zeolite which is effective for the catalysis of olefin hydration/etherification in said zones to provide alcohols(s) and ether(s). Useful zeolite catalysts include those disclosed in the prior art discussed above as well as in pending U.S. patent application Ser. Nos. 279,615; 139,566; 336,504; and 414,630 referred to above.

For purposes of this invention, the term "zeolite" is meant to include the class of porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst.

Representative of the zeolite olefin hydration/etherification catalysts which are preferred for use in the reactor system of this invention are zeolite Beta, zeolite X, zeolite L, zeolite Y, ultrastable zeolite Y (USY), dealuminized Y (Deal Y), mordenite, ZSM-3, ZSM-4, ZSM-5, ZSM-12, ZSM-20, ZSM-23, ZSM-38, ZSM-50, MCM-22 and mixtures of any of the foregoing.

Also included within the definition of the useful zeolites are crystalline porous silicoaluminophosphates such as those disclosed in U.S. Pat. No. 4,440,871, the catalytic behavior of which is similar to that of the aluminosilicate zeolites.

Zeolite Beta is described in U.S. Pat. No. Re. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat.No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-5 is described in U.S. Pat. No. Re. 29,948 (of original U.S. Pat. No. 3,702,886), to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-23 is described in U.S. Pat. No. 4,076,842, to which reference is made for the details of this catalyst.

Zeolite ZSM-35 is described in U.S. Pat. No. 4,016,245, to which reference is made for the details of this catalyst.

Zeolite ZSM-38 is described in U.S. Pat. No. 4,046,859, to which reference is made for the details of this catalyst.

Zeolite ZSM-50 is described in U.S. Pat. No. 4,640,829, to which reference is made for details of this catalyst.

Zeolite MCM-22 and the use of this zeolite to catalyze the reaction of olefin(s) with water to provide alcohol(s), ether(s) or mixtures thereof is disclosed in U.S. patent application Ser. No. 279,615 referred to above.

Zeolite MCM-22 is characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

Zeolite MCM-22 has a composition involving the molar relationship:

$$X_2O_3:(n)YO_2.$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area greater than 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It can, therefore, be used as an olefin hydration/etherification catalyst with acid activity without an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for olefin hydration/etherification. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstoms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409 for the PSH-3 compositions. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

The zeolite olefin hydration/etherification catalysts selected for use herein will generally possess an alpha value of at least about 1 measured at 538° C. "Alpha value", or "alpha number", is a measure of zeolite acidic functionality and is more fully described together with details of its measurement in 61 *J. Catalysis*, 390–396 (1980). Zeolites of relatively low acidity (e.g., zeolites possessing alpha values of less than about 200) can be prepared by a variety of techniques including (a) synthesizing a zeolite with a high silica/alumina ratio, (b) steaming, (c) steaming followed by dealuminization and (d) substituting framework aluminum with other trivalent metal species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Prior to their use as olefin hydration/etherification catalysts, the as-synthesized zeolite crystals should be subjected to thermal treatment to remove part or all of any organic constituent present therein. In addition, the zeolites should be at least partially dried prior to use. This can be done by heating the crystals to a temperature in the range of from about 200° to about 595° C. in an inert atmosphere, such as air, nitrogen, etc. and atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite olefin hydration/etherification catalysts herein, especially in their metal, hydrogen and ammonium forms, can be beneficially converted to other forms by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The original cations associated with the zeolites utilized herein can be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to VIII of the Periodic Table including, by way of example, iron, nickel, cobalt, copper, zinc, platinum, palladium, calcium, chromium, tungsten, molybdenum, rare earth metals, etc. These metals can also be present in the form of their oxides.

A typical ion-exchange technique involves contacting a particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251 and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

It can be advantageous to incorporate the above-described zeolite catalysts into some other material, i.e., a matrix or binder, which is resistant to the temperature and other conditions employed in the first stage reaction zone. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite olefin hydration/etherification catalyst can be composited with a porous metal oxide binder material such as alumina, titania, zirconia, silica, silica-alumina, silica-magnesia, silica-zirconia, silica-thoria, silica-beryllia, silica-titania, etc., as well as ternary oxides compositions such as silica-alumina-thoria, silica-alumina-zirconia, silica-alumina-magnesia, silica-magnesia-zirconia, etc. The binder material can be in the form of a cogel.

In some cases, it may be advantageous to employ as the binder material, one or more essentially non-acidic oxides of metals of Groups IVA and/or IVB of the Periodic Table of the Elements. Particularly useful are the oxides of silicon, germanium, titanium and zirconium with titanium and zirconium being preferred. Combinations of such oxides with other oxides including such relatively acidic oxides as alumina are also useful provided that at least about 40 weight percent, and preferably at least 50 weight percent, of the total metal oxide binder is one or a combination of the aforesaid Group IVA and/or Group IVB metal oxides. Thus, mixtures of oxides which can be used to provide the binder material herein include titania-alumina, titania-magnesia, titania-zirconia, titania-thoria, titania-beryllia, titania-silica-thoria, silica-alumina--zirconia, silica-alumina-magnesia, silica-titania-zirconia, and the like. It may be further advantageous to provide at least part of the Group IVA and/or IVB metal oxide binder, e.g., an amount representing from 1 to 100 weight percent and preferably from about 2 to about 60 weight percent of the total binder material, in colloidal form so as to facilitate the extrusion of the zeolite bound therewith.

The relative proportions of zeolite and metal oxide binder or other matrix material on an anhydrous basis can vary widely with the zeolite content ranging from between about 1 to about 99 weight percent, and more usually in the range of from about 5 to about 90 weight percent, of the dry composite.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

The following example is illustrative of the improved olefin hydration process of the present invention.

EXAMPLE

This example illustrates a simulated operation of the reactor system of FIGS. 2A-B in carrying out the catalytic hydration of propylene admixed with propane in the presence of zeolite MCM-22 to provide a product largely comprising isopropyl alcohol.

The temperature, pressure and weight hourly space velocity (WHSV) in grams of propylene per grams of catalyst per hour conditions in the various zones of the reactor system of FIGS. 2A-B and the composition within these zones is set forth below:

| | Zones of the Reactor System of FIG. 2 | | | |
|---|---|---|---|---|
| | Feed Preheat Zones 14, 16 Near Extreme Top and Bottom Regions of the Reactor | Feed Preheat Zones 14, 16 Near Middle Region of the Reactor | Middle Region 25 of the Reactor | Outlet Zones 20 and 22, 22' |
| Conditions | | | | |
| Temperature, °F. | 95 | 300 | 300 | 330 |
| Pressure, psig | 2000 | 2000 | 2000 | 2000 |
| WHSV, hr$^{-1}$ | 0.25 | 0.25 | 0.25 | 0.25 |
| Composition, Wt. fraction | | | | |
| Propylene | 0.46 | 0.46 | 0.42 | 0.17 |
| Isopropyl Alcohol | 0.18 | 0.18 | 0.18 | 0.18 |
| Water | 0.09 | 0.09 | 0.08 | 0.04 |
| Diisopropyl Ether | — | — | 0.04 | 0.31 |
| $C_6 + C_9$ | — | — | 0.01 | 0.03 |
| Propane | 0.27 | 0.27 | 0.27 | 0.27 |

What is claimed is:

1. A reactor system for conducting a chemical conversion reaction which comprises:
   a) a first reactor sub-unit for providing a first fluid flow path and possessing a feed temperature modification zone and a reaction zone, said reaction zone of said first reactor sub-unit containing a quantity of a zeolite catalyst;

b) a second reactor sub-unit providing a second fluid flow path and possessing a feed temperature modification zone and a reaction zone, said reaction zone of said second reactor sub-unit containing a quantity of a zeolite catalyst and wherein said reaction zone of said second reactor sub-unit is separate from said reaction zone of said first reactor sub-unit such that there is no contact between reactants in said reaction zone of said second reactor sub-unit and reactants in said reaction zone of said first reactor sub-unit;

c) first heat transfer means for either transferring heat from the reaction zone of the first reactor sub-unit to the feed temperature modification zone of the second reactor sub-unit when the reaction occurring in said reaction zone is exothermic or transferring heat to the reaction zone of the first reactor sub-unit from the feed temperature modification zone of the second reactor sub-unit when the reaction occurring in said reaction zone is endothermic; and d) second heat transfer means for either transferring heat from the reaction zone of the second reactor sub-unit to the feed temperature modification zone of the first reactor sub-unit when the reaction occurring in said reaction zone is exothermic or transferring heat to the reaction zone of the second reactor sub-unit from the feed temperature modification zone of the first reactor sub-unit when the reaction occurring in said reaction zone is endothermic.

2. The reactor system of claim 1 wherein the feed temperature modification zone of first reactor sub-unit (a) is adjacent to, and shares a common reactor wall with, the reaction zone of second reactor sub-unit (b) and the feed temperature modification zone of second reactor sub-unit (b) is adjacent to, and shares a common reactor wall with, the reaction zone of first reactor sub-unit (a).

3. The reactor system of claim 1 wherein the feed temperature modification zone of each reactor sub-unit contains a packing material to promote heat transfer to or from the feed introduced therein.

4. The reactor system of claim 1 wherein the first and/or second heat transfer means comprises a plurality of heat conducting rod elements traversing feed temperature modification and reaction zones.

5. The reactor system of claim 1 wherein the first and/or second heat transfer means comprises a conduit for transferring a third fluid heat conducting medium from or to the reaction zone of one reactor sub-unit to or from the feed temperature modification zone of the other reactor sub-unit.

6. An olefin hydration reactor system which comprises:

a) a first olefin hydration reactor sub-unit for providing a second fluid flow path possessing a feed preheating zone and an olefin hydration reaction zone containing olefin hydration catalyst;

b) a second olefin hydration reactor sub-unit for providing a second fluid flow path possessing a feed preheating zone and an olefin hydration reaction zone containing olefin hydration catalyst and wherein said olefin hydration reaction zone of said second olefin hydration reactor sub-unit is separate from said olefin hydration reaction zone of said first olefin hydration reactor sub-unit such that there is no contact between reactants in said olefin hydration reaction zone of said second olefin hydration reactor sub-unit and reactants in said olefin hydration reaction zone of said first olefin hydration reactor sub-unit;

c) first heat transfer means for transferring heat from the olefin hydration reaction zone of the first olefin hydration reactor sub-unit to the feed preheating zone of the second olefin hydration reactor sub-unit; and, d) second heat transfer means for transferring heat from the olefin hydration reaction zone of the second olefin hydration reactor sub-unit to the feed preheating zone of the first olefin hydration reactor sub-unit.

7. The olefin hydration reactor system of claim 6 wherein the feed preheating zone of first reactor sub-unit (a) is adjacent to, and shares a common reactor wall with, the olefin hydration reaction zone of second olefin hydration reactor sub-unit (b) and the feed preheating zone of second olefin hydration reactor sub-unit (b) is adjacent to, and shares a common reactor wall with, the olefin hydration reaction zone of second reactor sub-unit (a).

8. The reactor system of claim 6 wherein the feed preheating zone of each olefin hydration reactor sub-unit contains a packing material to promote heat transfer to the feed introduced therein.

9. The reactor system of claim 6 wherein the first and/or second heat transfer means comprises a plurality of heat conducting rod elements traversing feed preheating and olefin hydration reaction zones.

10. The reactor system of claim 6 wherein the first and/or second heat transfer means comprises a conduit for transferring a third fluid heat conducting medium from the olefin hydration reaction zone of one olefin hydration reactor sub-unit to the feed preheating zone of the other olefin hydration reactor sub-unit.

* * * * *